(12) United States Patent
Horn-Ranney et al.

(10) Patent No.: US 10,357,591 B2
(45) Date of Patent: Jul. 23, 2019

(54) SELECTIVELY POLYMERIZABLE COMPOSITIONS AND METHODS OF USE IN VIVO

(71) Applicant: The Administrators of the Tulane Educational Fund, New Orleans, LA (US)

(72) Inventors: Elaine Horn-Ranney, New Orleans, LA (US); Parastoo Khoshakhlagh, New Orleans, LA (US); Michael Moore, New Orleans, LA (US); Jesse Ranney, New Orleans, LA (US)

(73) Assignee: Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/583,708

(22) Filed: Dec. 28, 2014

(65) Prior Publication Data
US 2015/0112244 A1 Apr. 23, 2015

Related U.S. Application Data

(63) Continuation of application No. PCT/US2013/048385, filed on Jun. 28, 2013.
(Continued)

(51) Int. Cl.
*A61K 9/00* (2006.01)
*A61L 27/14* (2006.01)
(Continued)

(52) U.S. Cl.
CPC ............ *A61L 27/14* (2013.01); *A61K 38/385* (2013.01); *A61L 27/20* (2013.01); *A61L 27/52* (2013.01);
(Continued)

(58) Field of Classification Search
CPC ....................................................... A61L 27/14
See application file for complete search history.

(56) References Cited

U.S. PATENT DOCUMENTS

| | | | |
|---|---|---|---|
| 2005/0038471 A1* | 2/2005 | Chan | A61F 9/0079 606/214 |
| 2005/0176905 A1 | 8/2005 | Moon et al. | |

(Continued)

FOREIGN PATENT DOCUMENTS

| | | |
|---|---|---|
| JP | 2003531647 A | 10/2003 |
| JP | 2010005230 A | 1/2010 |
| WO | 2007035296 A2 | 3/2007 |

OTHER PUBLICATIONS

Sheppard, Review of salicylate-induced hearing loss, neurotoxicity, tinnitus and neuropathophysiology, Acta Otorhinolaryngologica Italica, 2014, 34, 79-93.*

(Continued)

*Primary Examiner* — Paul W Dickinson
(74) *Attorney, Agent, or Firm* — Edna Vassilovski

(57) ABSTRACT

Otologic materials and methods are provided. For example, a cell-adhesive, biodegradable hydrogel scaffold loaded with time-released drugs for repairing chronic tympanic membrane perforations is disclosed, methods of making same and administering same are provided. This hydrogel may promote vascular in-growth and epithelial cell growth of the tympanic membrane with the purpose of closing the perforation and providing a barrier between the external and middle ear. The hydrogel is initially a liquid polymer that only gels upon exposure to specific conditions, such as exposure to light. This scaffold may simultaneously induce repair of the tympanic membrane while preventing or alleviating middle ear infection, thus filling a void in current tympanic membrane perforation therapies.

21 Claims, 3 Drawing Sheets

Related U.S. Application Data

(60) Provisional application No. 61/665,639, filed on Jun. 28, 2012.

(51) Int. Cl.
| | |
|---|---|
| *A61L 27/20* | (2006.01) |
| *A61L 27/52* | (2006.01) |
| *A61L 27/56* | (2006.01) |
| *A61L 27/54* | (2006.01) |
| *A61K 38/38* | (2006.01) |
| *A61N 5/06* | (2006.01) |

(52) U.S. Cl.
CPC ............. *A61L 27/54* (2013.01); *A61L 27/56* (2013.01); *A61N 5/062* (2013.01); *A61L 2430/14* (2013.01)

(56) References Cited

U.S. PATENT DOCUMENTS

| | | | |
|---|---|---|---|
| 2006/0024826 A1 | 2/2006 | Bonassar et al. | |
| 2006/0287410 A1* | 12/2006 | Chudzik | A61K 6/0017 523/116 |
| 2010/0069927 A1* | 3/2010 | Clark | A61K 31/00 606/151 |
| 2010/0285094 A1* | 11/2010 | Gupta | A61L 15/60 424/429 |
| 2011/0110987 A1 | 5/2011 | Kanemaru | |

OTHER PUBLICATIONS

Park, A.H. et al., "Crosslinked hydrogels for tympanic membrane repair," Otolaryngology—Head and Neck Surgery, 2006, vol. 135, pp. 877-883.

Leach, Jennie Baier et al., "Photocrosslinked hyaluronic acid hydrogels: Natural, biodegradable tissue engineering scaffolds," Biotechnology and Bioengineering, Wiley & Sons, Hoboken, NJ, US, (Jun. 5, 2003), vol. 82, No. 5, pp. 578-589.

Brian G. Amsden et al., "Methacrylated Glycol Chitosan as a Photopolymerizale Biomaterial," Biomacromolecules, Dec. 1, 2007), vol. 8, No. 12, pp. 3758-3766.

Bing Mei Teh et al., "Tissue Engineering of the Tympanic Membrane," Tissue Engineering: Part B, vol. 19, No. 2, 2013, pp. 116-132.

* cited by examiner

SELECTIVELY POLYMERIZABLE COMPOSITIONS AND METHODS OF USE IN VIVO

CROSS-REFERENCE TO RELATED APPLICATIONS

This application is a continuation of International Application No. PCT/US2013/048385, filed Jun. 28, 2013, which claims benefit of priority to U.S. Provisional Patent Application No. 61/665,639, entitled, "SELECTIVELY POLYMERIZABLE HYDROGEL FOR USE AS A MULTI-PURPOSE SURGICAL SCAFFOLD WITH DRUG-DELIVERY CAPABILITIES," filed Jun. 28, 2012, both of which are incorporated herein by reference in their entirety.

BACKGROUND

In the US alone, over 1,000,000 procedures to insert pressure equalizing tubes (PETs) in the tympanic membrane (TM) are performed each year. These tubes allow fluid from middle ear infections to drain from the middle ear to the external ear canal, thus relieving the pain from pressure build-up. Chronic TM perforations are generally thought to occur when PETs are left in the TM for extended periods of time. For PETs left in the TM for 18 months or less, the chronic TM perforation rate is between 1-5%. However, some patients require PETs for 2 years or longer—the rate of chronic TM perforation for this group is about 9%.

To treat chronic TM perforations, the fibrous tissue around the perforation is abraded to induce an inflammatory response. If the perforation is small such as about 20% or less of the cross-sectional area of the TM, the perforation can be packed with either paper or fat taken from the earlobe. Larger perforations require a more substantial packing material, such as autografts of cartilage or fascia, surgical gelatin, or a synthetic polymer patch. All of these therapies require some kind of surgery, and the success rate of the therapy is highly dependent upon the skill of the surgeon.

There are several commercial otologic packing products available in the market. Pfizer manufactures Gelfoam®, a type of surgical gelatin obtained from pigs used as a packing material for the middle ear after surgery. Typically, once the middle ear has been cleared of fluid via surgery, Gelfoam® is used to fill the void in the middle ear. Gelfoam® liquefies when hydrated, and is degraded and cleared easily by the body. In addition to acting as a barrier between the middle and external ear while the TM perforation heals, it also provides a surface to which autografts or patches may adhere. However, due to the nature of porcine gelatin, some patients may be allergic to this material.

Medtronic ENT/Xomed manufactures Merogel®, a fibrous packing material similar to that of Gelfoam®, but is instead made of hyaluronic acid. Merogel® turns into a gel when hydrated, and is easily degraded. It has the same properties as Gelfoam®, but without the risk of allergic reaction due to porcine gelatin. Like Gelfoam®, it is used to pack the middle ear prior to insertion of an autograft or patch, and is not used as a stand-alone treatment.

Medtronic ENT/Xomed also manufactures EpiDisc™, a porous hyaluronic patch intended to repair tympanic membranes. It is biodegradable and induces both epithelial cell growth and vascular in-growth of the tympanic membrane. However, to use this patch, it must be trimmed to the size of the perforation and inserted surgically. Occasionally, the patch fails to adhere completely to the native tissue or packing material in the middle ear, resulting in additional surgery to replace the patch.

None of the current products available for repairing TM-perforation deliver drugs directly to the middle ear. The current method for delivering drugs directly to the middle ear is with eardrops. The main drug used for treating ear infections (ciprodex) stings when applied. This is an important factor to consider when the majority of the patients treated for ear infections are children under the age of 10.

To date, no photopolymerizable hydrogels have been used as scaffolds for otologic use, in which the liquid polymer is applied to the desired site prior to curing. Blue light-polymerizable materials are used in the dental field, but none of the components apply to otologic use. Using a scaffold that is initially a liquid and only forms a scaffold upon exposure to specific conditions is a total departure from current and traditional therapies for repairing TM perforations.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

SUMMARY

The present invention provides selectively polymerizable materials and methods of use in vivo. For example, the present invention provides selectively polymerizable otologic materials and methods of use of the materials in the ear of a patient.

In some embodiments, the otologic materials are a liquid pre-polymer composition comprising at least a first polymer (capable of selectively curing/selectively assembling into a polymer matrix under defined conditions in the ear of a patient) and a solvent. In some embodiments, the otologic materials are a liquid pre-polymer composition comprising at least a first polymer, a solvent and an initiator which when activated in situ in the ear of a patient, results in the repairing or aiding in the repair of a tympanic membrane perforation. In further embodiments, the liquid pre-polymer composition also comprises a therapeutic composition. In some further embodiments, the polymer matrix has a porosity and an average pore size compatible with releasing the therapeutic composition over a desired time period. In some embodiments the polymer matrix may be in the form of a gel such as a hydrogel, and may have a stiffness sufficient to function as a scaffold on which epithelial cells of the tympanic membrane can migrate, adhere and grow. In some embodiments, the at least first polymer is functionalized such that the resulting polymer matrix has a cell-binding domain, for example, which may improve cell migration and adhesion. In some embodiments, the initiator is a photoinitiator which is activated by light, for example visible, ultraviolet, infrared, or blue light. In some embodiments, the at least first polymer is chosen from polyethylene glycols (PEGs) and polysaccharides such as methacrylated chitosan, hyaluronic acid and methacrylated hyaluronic acid. In further embodiments, the at least first polymer is one or more PEGs. In other embodiments, the at least first polymer is a methacrylated chitosan and hyaluronic acid. In alternative embodiments, the at least first polymer is a methacrylated chitosan and a methacrylated hyalauric acid. In yet other embodiments, the at least first polymer is a PEG in combination with at least one of a chitosan or a hyaluronic acid.

Some embodiments of materials according to this disclosure, for example some embodiments of photo-curable hydrogel materials according to this disclosure, compare to certain commercial otologic products as shown in Table 1 below:

TABLE 1

| Product | Material | Function | Surgery required? | Drug delivery? |
|---|---|---|---|---|
| GelFoam ® (Pfizer) | Porcine gelatin | Packing | Yes | No |
| MeroGel ® (Medtronic) | Hyaluronic acid | Packing | Yes | No |
| EpiDisc ™ (Medtronic) | Hyaluronic acid | Patch | Yes | No |
| An exemplary embodiment of the present invention | Polyethylene glycol/chitosan/hyaluronic acid | Patch | No | Yes |

In some embodiments, the otologic methods include treating a perforation of the tympanic membrane by administering a liquid pre-polymer composition comprising at least a first polymer, a solvent and optionally an initiator (for example if required to activate the assembly of the at least first polymer into a polymer matrix) to the site of the perforation, and activating the composition (for example activating the initiator) resulting in the liquid composition assembling into a polymer matrix, such as a hydrogel. In further embodiments, the liquid composition also includes a therapeutic composition. In some embodiments, the method involves administering a sufficient amount of the liquid composition to at least cover the perforation. In some embodiments, wherein the composition comprises a photoinitiator, activating involves exposing the liquid composition to light such as blue light, visible light, infrared (IR) light or ultraviolet (UV) light. In some embodiments, activating involves exposing the composition to a change of temperature or a change of pH or a change of ion concentration for example such as may be found in the natural environment of the ear. In some embodiments, activating involves exposing the liquid composition to chemical radical initiators. Other methods of activating the liquid compositions are also within scope of this disclosure provided they are biocompatible and suitable for the specific purpose, such as use in repairing perforations of tympanic membranes, or such as timed release delivery of drugs in the ear.

In some embodiments, the otologic methods involve enhancing existing otologic packing materials by administering liquid pre-polymer compositions described herein to the packing materials and curing or assembling the liquid pre-polymer compositions after administration. In some embodiments, the otologic packing materials are first administered to a desired site in a patient's ear prior to administering the liquid pre-polymer compositions.

The methods and materials may accomplish one or more of the following objects:

Aid in the repair of chronic TM perforations of variable size, for example by providing a scaffold for new cell growth and releasing drugs in a time-dependent manner. The scaffold may be biodegradable, hydrophilic, non-carcinogenic, non-cytotoxic, non-ototoxic, and polymerizes only when exposed to a specific set of conditions, such as blue light, UV light, IR light or visible light, chemical radical initiators, or specific conditions of pH, ion concentration, temperature.

Resolve some of the issues with current TM perforation therapies, including adherence of the scaffold to the surrounding tissue, and direct delivery of drugs to the middle ear to prevent recurring infection.

Fill the area of a perforation in a tympanic membrane without the need for autografts or patches cut to the exact dimensions of the perforation, for example by delivering the scaffold in curable liquid form to the site of perforation. Such an approach may have the advantage of removing the skill of the surgeon as a factor for success rate of the procedure, for example because the compositions are configured to be viscous enough not to fall through the perforation into the middle ear.

Forming a hydrogel scaffold stiff enough to retain its shape, adhesive enough to provide a scaffold on which epithelial cells of the TM can migrate and grow, and/or remain in the place it was assembled (for example due to is stiffness and adhesive properties). Drugs loaded into the liquid polymer may be confined to the pores of the scaffold upon assembly, for example with light, and are released as the cells of the TM degrade the cross-links of the scaffold.

Curing or assembling the scaffold using a photoinitiator or based on ionic strength, or using chemical catalysts or chemical groups that recognize each other and bind together, such as "click" reagents.

Deliver drugs directly to the middle ear in order to prevent or alleviate a recurrent infection. For example, the materials and methods may result in releasing drugs in a controlled and sustained manner for a predetermined length of time. For example, the dosage of the drug may be controlled by the degradation rate of the scaffold and the amount loaded into the liquid polymer. Such an approach may have an advantage over eardrops, which can only release drugs to the TM and middle ear in a single burst, thus requiring timed reapplication over the course of the treatment. Such an approach may also provide a more efficient method for delivering more exact quantities of drug to the middle ear over current therapies. Such an approach may also enhance the effect of the drugs as compared to current therapies.

Deliver drugs directly to the middle ear of patients, and for example children, to allow easier administration of otological treatments.

Deliver drugs to the vitreous.

Provide physicians an option to use a selectively-polymerizable scaffold for sustained drug release, for example where such an approach may be beneficial, whether in a clinical or surgical setting.

Enhance the features of existing products and treatments by using the materials and methods in accordance with this disclosure in conjunction with one or more of existing treatments.

Form a scaffold such as by using one or more of polyethylene glycol (PEG), chitosan, hyaluronic acid, and/or analogs or derivatives thereof as a scaffold.

Form a functionalized scaffold with a cell-binding domain, for example to improve cell adhesion and migration on the scaffold.

Design a target drug time release profile for the polymer matrix, for example through use of a particular amount of PEG.

While the disclosure provides certain specific embodiments, the invention is not limited to those embodiments. A person of ordinary skill will appreciate from the description herein that modifications can be made to the described embodiments and therefore that specification is broader in scope than the described embodiments. All examples are therefore non-limiting.

DETAILED DESCRIPTION

Introduction

Figure 1:
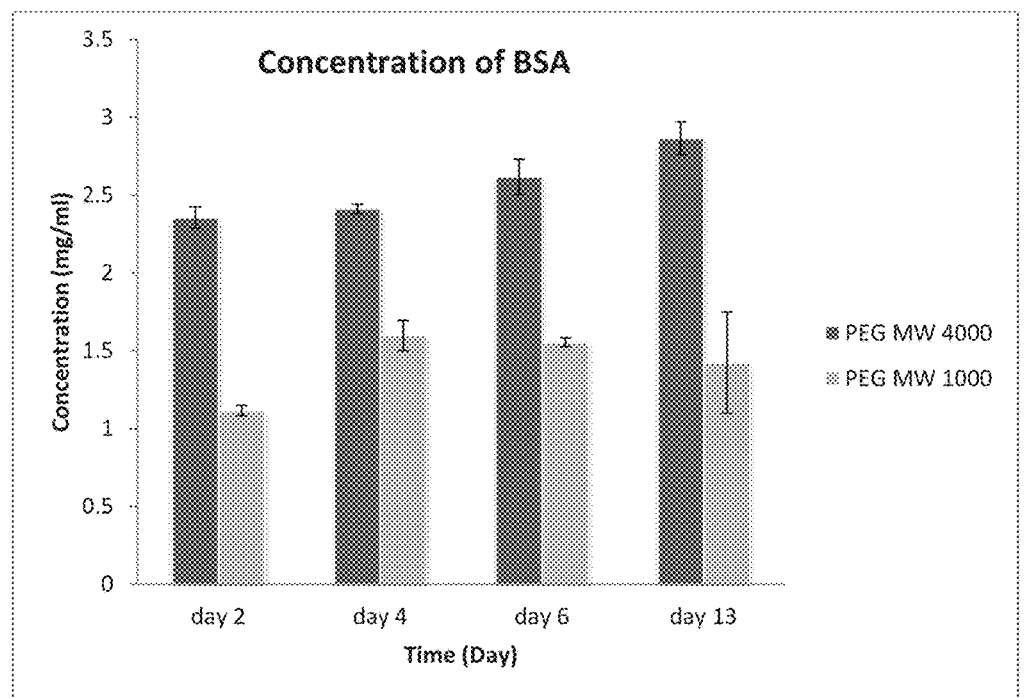
FIG. 1 is a graph illustrating a quantification of bovine serum albumin released from exemplary PEG hydrogels of two different molecular weights over time.

Detailed descriptions of one or more embodiments are provided herein. It is to be understood, however, that the present invention may be embodied in various forms. Therefore, specific details disclosed herein are not to be interpreted as limiting.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited. Therefore, for example, the phrase "an embodiment with PEG MW 4000" means "an embodiment with substantially PEG MW 4000" so long as a precise molecular weight is not necessary for the embodiment to perform its function.

The term "about" is meant to account for variations due to experimental error. All measurements or numbers are implicitly understood to be modified by the word about, even if the measurement or number is not explicitly modified by the word "about."

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

Where ever the terms "a" or "an" are used, "one or more" is understood, unless such interpretation is nonsensical in context.

The term "liquid pre-polymer composition" or alternatively "pre-polymerization solution" mean the same thing and refer to a composition (comprising at least one polymer) which is capable of being activated to assemble into a more viscous form but that has not yet so assembled. A "liquid pre-polymer composition" need not be liquid but only less viscous than its assembled form. In some embodiments, a "liquid pre-polymer composition" is sufficiently viscous such that it can be positioned to cover a perforation without falling through to the middle ear cavity.

The terms "scaffold" refers to a "polymer matrix" having properties compatible with treating a perforation of the tympanic membrane such as by having a stiffness compatible with the migration and growth of epithelial cells on or in the scaffold, and/or by having a porosity compatible with releasing a therapeutic composition, which was part of the liquid pre-polymer composition for example according to a desired time-dependent profile.

The terms "polymerization," "gelation," "crosslinking," "assembling" and "curing" mean the transition of materials, such as otologic materials, according to this disclosure from a liquid pre-polymer to a harder or tougher form such as a gel, solid, or interpenetrating polymer network, which may result from activating the materials such as by adding an assembling agent or curing agent (and activating the agent by for example light, pH, body fluids, temperature, other chemical changes, etc.) or having the pre-polymer assemble or cure through existing natural conditions (for example activating the assembly of the polymers in the liquid pre-polymer composition into a polymer matrix due to the presence of body fluids or existing conditions for example of pH or temperature or ion concentration at the site of administration).

Reference to a polymer, such as "chitosan," "polyethylene glycol," or "hyaluronic acid," (as well as reference to those polymers in plural, such as "chitosans," "polyethylene glycols," and "hyaluronic acids") is understood to be reference to a class of polymers, unless in context it is clear that only the basic (backbone) polymer is intended. In other words, the term "chitosan" means chitosan and its derivatives and analogs (for example methacrylated chitosan), the term "polyethylene glycol" refers to polyethylene glycol, its derivatives and analogs, and the term "hyaluronic acid" means hyaluronic acid, its derivatives and analogs.

The present disclosure provides otologic materials and methods. In some embodiments, the otologic materials and methods are directed at treating perforations of the tympanic membrane (TM), including chronic perforations of the TM. In some embodiments, the otologic materials comprise a liquid pre-polymer composition that is cured/assembled in situ resulting in a polymer matrix, for example in the form of a hydrogel scaffold. In some further embodiments, the otologic materials are loaded with drugs, for example for direct delivery to the middle ear to prevent infection, for example recurring infection. In some embodiments, the methods comprise administering the otologic liquid pre-polymer materials to a desired site in a patient's ear and curing/assembling the materials in situ. In some embodiments, the methods comprise administering the liquid pre-polymer materials to an otologic packing material and curing/assembling the liquid pre-polymer materials after administration to the packing material.

Materials

Materials according to this disclosure include liquid pre-polymer compositions, which can be cured/assembled into a polymer matrix. The materials also include the resultant polymer matrix itself. In some embodiments, the polymer matrix is a scaffold having sufficient stiffness and/or tackiness (for example as a result of functional groups providing cell adhesion domains) such that epithelial cells in the TM can migrate into and/or onto the scaffold and adhere and/or grow. In some further embodiments, the polymer matrix or scaffold eventually degrades in situ, i.e. is biodegradable, for example after the epithelial cells have grown sufficiently to repair the perforation. In alternative or further embodiments, the liquid pre-polymer composition is designed to cure/ assemble into a polymer matrix or scaffold having a porosity and average pore size compatible with loading the resultant polymer matrix or scaffold with a therapeutic agent. In additional embodiments, the porosity and average pore size are chosen to provide a desired time-dependent release profile for the loaded therapeutic agent.

In general, the otologic materials according to this disclosure are initially a pre-polymer liquid composition for easy administration to a desired site in a patient's ear, and are configured to cure/assemble into a polymer matrix in vivo in the ear of a patient upon activation. Accordingly, in general, the liquid pre-polymer compositions include one or more polymers capable of selectively assembling into a polymer matrix at a desired time under specific conditions (for example conditions found in the ear, such as the middle ear), and a solvent. Thus, for example, the liquid pre-polymer composition may include an initiator, such as a photoinitiator, and the polymers in the liquid pre-polymer composition may be selectively assembled by exposing the composition to light thereby activating the initiator resulting in curing/assembling the pre-polymer composition into a polymer matrix. As one example, the polymers may be functionalized with methacrylate groups to give them cross-linkability, and riboflavin (a non-carcinogenic, non-cytotoxic photoinitiator) may be added to the liquid pre-polymer composition to initiate the cross-linking of the methacrylate groups in the presence of light. In general, the composition ingredients are chosen to be biocompatible and suitable for use in the ear, for example the external auditory canal, middle ear, or both. In some embodiments, the ingredients are chosen such that the resultant polymer matrix is biodegradable, and may be processed and cleared by the body. For example, the components chosen are biodegradable, biocompatible, and may be expelled by the kidneys.

In some embodiments, the liquid pre-polymer composition includes at least a first polymer capable of assembling into a polymer matrix, e.g. capable of being cured/assembled such as capable of reacting under defined conditions to form a polymer matrix. For example, the polymer may include functional groups that can associate to form a network, for example through formation of covalent bonds, physical bonds, or combinations of both. Without wishing to be bound by theory, the functional groups on the polymer may determine how it can assemble into a polymer matrix. In some embodiments, for example where the polymer is functionalized with methacrylate groups (for example chitosan or hyaluronic acid), an initiator may be used to crosslink the polymers. In another embodiment, changes in pH, temperature, or ion concentration initiate spontaneous assembly of the polymer matrix.

Examples of potentially suitable polymers include the following, and/or derivatives and analogs thereof (for example derivatives include polymers listed below which are modified to include functional groups that can associate to form a network, and/or for example the polymers listed below may be functionalized to achieve a desired goal such as providing cell adhesion domains): polyethylene glycols (PEGs); polysaccharides; poly(lactic acids); polyurethanes; poly(propylene glycols); poly(propylene fumarate-co-ethylene glycol); poly(hydroxyethyl methacrylate); polyvinylpyrrolidones; poly(2-acrylamido-2-methyl-1-propanesulfonic acid); polyvinyl alcohols; polypeptides; polyacrylates; agaroses; poly(hydroxyethylmethacrylates); polyesters; gelatins; celluloses; alginates; k-carrageenans; pectins; starchs; dextrans; chondroitin sulfates; and certain proteins such as collagen, fibrin, laminin and heparin. In some embodiments such as embodiments wherein the polymer matrix may degrade, components are chosen to result in degradation products that are not ototoxic.

In some embodiments, the liquid pre-polymer composition comprises a polymer chosen from polyethylene glycols, chitosans, hyaluronic acids, and combinations thereof. In some embodiments, the specific polymers, mixture of polymers, and relative amount of polymers may be chosen to result in a polymer matrix or scaffold that is hydrophilic and biodegradable. In some embodiments, the polymer matrix is produced from PEG or combinations of PEG alone, such as poly(ethylene glycol) diacrylate of molecular weight 1000 or poly(ethylene glycol) diacrylate of molecular weight 4000 or combinations thereof. In some embodiments, the polymer matrix is produced from methacrylated chitosan alone, methacrylated hyaluronic acid alone, nethacrylated chitosan and methacrylated hyaluronic acid together, methacrylated chitosan and hyaluronic acid together, or PEG in combination with methacrylated chitosan, methacrylated hyaluronic acid, hyaluronic acid or combinations thereof.

In some embodiments, the polymers may be chemically modified, or purchased as a chemically modified version. In some embodiments, the polymers are chemically modified (or purchased as a chemically modified version) for one or more of the following reasons: to permit or facilitate the formation of the polymer matrix, to improve gelation, cell adhesion, drug release, protein adhesion, degradation rate and profile, drug loading/incorporation, surface properties, mechanical properties, hydrophillicity, etc. For example, the polymers may be functionalized with groups that cells can bind to such as cell-binding domains of amino acids, ligands, proteins, or other molecules intended to improve cell and protein adhesion to the scaffold. As one example, the amino acid sequence arginine-glycine-aspartic acid-serine (RGDS) may be incorporated into a PEG to increase cell adhesion.

In further embodiments, the molecular weight of the polyethylene glycol (PEG) may range from about 100 to about 1,000,000 g/mol. In some embodiments, the molecular weight of the chitosan may range from about 100 to about 1,000,000 g/mol, with deacylation ranging from about 0 to about 100%. In some embodiments, the molecular weight of the hyaluronic acid may range from about 100 to about 1,000,000 g/mol. In certain embodiments, any of the ranges above may be incorporated in a hydrogel in some manner. In some embodiments, the chitosan used for the polymer matrix or scaffold may be either purchased or acquired from shellfish.

Chitosan is a suitable polymer alone or in combination with other polymers because it is derived from naturally occurring sources and can be modified such that it is capable of crosslinking into a polymer matrix. When crosslinked it is tacky and sticks to epithelial cell surfaces. Cells are able to grow through and degrade a chitosan network. Due to the functional groups on the polysaccharide backbone of chitosan, it can be used as an antibacterial agent. Though chitosan is derived from chitin found in shellfish, it does not possess any of the allergy-inducing characteristics.

Hyaluronic acid is also a suitable polymer alone or in combination with other polymers because is it also derived from naturally-occurring sources. It is used in many medical applications, as its functional groups make it an excellent substrate for cell growth. Hyaluronic acid can also be modified to be able to crosslink into a polymer matrix.

PEG (e.g. PEG diacrylate) is a suitable polymer alone or in combination with other polymers because it is available in a variety of molecular weights, from relatively short polymer chains to relatively long polymer chains, facilitating control of the degradation and drug release rates of the resulting polymer matrix. In some embodiments, PEG is used in combination with other polymers such as chitosan or hyaluronic acid in order to result in a scaffold to which cells can adhere.

However, other polymers listed above may also be used/modified in place of chitosan, hyaluronic acid and/or PEG. In general some factors to consider in choosing suitable polymers (derivatives and analogs thereof) include mechanical properties, drug release, polymer degradation, and cell growth and viability. With respect to mechanical properties, this parameter depends on the polymer backbone and crosslink density. For example, in the case of a hydrogel polymer matrix, formed by exposing the liquid solution to light, a person of skill can balance polymer concentration, initiator concentration, irradiation time, and output to obtain a cross-linked gel with a desired stiffness. With respect to drug release, the mechanical properties of the material influence the release of drugs from the material, with release rate being related to the pore size of the material. With respect to polymer degradation, this parameter depends on the structure of the polymer, polymer concentration and environmental factors, such as cells and enzymes. Both chitosan and hyaluronic acid (as well as PEG) are able to be degraded by cells and enzymes found in the tympanic membrane environment. With respect to cell growth and viability, this depends on the functional groups of the polymer backbone and the stiffness of the polymer matrix. Epithelial cells are thought to prefer stiff substrates, accordingly in some embodiments the polymer or polymer blend is chosen to yield a stiff gel. In some embodiments, a stiff gel is a gel with a higher elastic modulus than its pre-polymerized form. In some embodiments, a stiff gel is one that is sufficiently stiff that when positioned to cover a perforation it won't fall through the perforation into the middle ear. Additionally, chitosan and hyaluronic acid may provide functional groups to allow cells to adhere to the polymer network.

The liquid pre-polymer composition may also include an initiator if required to initiate assembly of the polymers into a polymer matrix. In some embodiments, it is desirable for the initiator to be non-carcinogenic and non-cytotoxic. In some embodiments, the initiators may include systems that are cytocompatible, light-sensitive, free radical initiators often used to cure/assemble methacrylate- and acrylate-containing polymer gels. For example, the composition may include a photoinitiator if applicable to cause crosslinking of the polymers in solution. For example, the photoinitiator system may be used to initiate a free-radical reaction to induce gelation of the scaffold, with the light having a wavelength ranging from about $10^{-8}$ to about $10^{-3}$ m (ultraviolet through infrared). In some embodiments, for example those used in the vitreous, a photoinitiator that is activated within the visible light spectrum may be chosen. In other embodiments, such as embodiments for otologic purposes, a photoinitiator that is activated by UV light or blue light may be chosen. Some examples of suitable photoinitiators include Irgacure 2959 if curing or activating with UV light-sensitive compounds, eosin Y in conjunction with 1-vinyl-2 pyrrolidinone and treithanolamine if curing or activating with visible light-sensitive compounds, and camphorquinone and/or riboflavin 5'-monophosphate sodium salt if curing or activating with blue light. In some embodiments, the forming polymer matrix/scaffold/hydrogel is designed to remain translucent as it polymerizes to facilitate light permeating the entire depth of the forming matrix/scaffold/gel and liquid pre-polymer solution.

In some embodiments, the liquid polymer composition of the scaffold may be loaded (at least partially) with drugs or other substances, (e.g., antibiotics, antimicrobials, growth factors, antifungals, anti-inflammatories, analgesics, steroids, cytokines, proteins, pain relievers and biologically active small molecules, etc.) prior to curing or activating with light into a gel or solid. The scaffold may be loaded with antibiotics such as fluoroquinolones, aminoglycosides, and polymixins. The scaffold may be loaded with antifungal agents such as clotrimazole, nystatin, and tolnaftate. The scaffold may be loaded with growth factors, such as fibroblast growth factors, vascular endothelial growth factors, transforming growth factors, epidermal growth factors, keratinocyte growth factors, platelet-derived growth factors. The scaffold may be loaded with other molecules, such as interleukins and additional protein treatment or other curing treatment. To achieve this purpose of loading a scaffold/use of a scaffold for drug delivery, the scaffold may be in the form of a hydrogel. In some embodiments, hydrogels are hydrophilic polymer networks having a water content higher than about 90%, providing the hydrogels with an enhanced ability to encapsulate cells, bioactives and drug molecules as compared to materials that are not hydrogels.

A person of skill understands how to load a drug into a polymer network, for example by mixing the drug with the pre-polymerization solution resulting later in the drug being confined to the pores of the polymer network upon assembly. See, e.g., Bhattarai, N. et al. Adv. Drug Deliv. Rev. (2010) 62:83-89, and Han, J. et al. Int. J. Biol. Macromol. (2009) 44:229-235. It is also within the skill of the art to create a system with a desired controlled drug release profile. The release of the drug relates to the pore size of the scaffold as well as the degradation rate of the scaffold. See, e.g., id. To change the pore size of the scaffold, for example, the concentration of polymer in solution may be changed, as well as the number of crosslinking sites on the polymer backbone. Altering these parameters changes the crosslinking density of the polymer network, and effectively the pore size. The scaffold also has a measurable stiffness associated with the polymer backbone, crosslink density, polymer concentration and initiator concentration.

In some embodiments, the liquid pre-polymer compositions therefore comprise at least a first polymer (which is capable of selectively assembling into a polymer matrix under defined conditions in the ear of a patient) and a solvent. In further embodiments, the liquid pre-polymer compositions comprise at least a first polymer, an initiator and a solvent. In some embodiments, the liquid pre-polymer compositions comprise at least a first polymer and at least a second polymer and a solvent. In some embodiments, the liquid pre-polymer compositions comprise at least a first polymer and at least a second polymer, an initiator and a solvent. In some embodiments, the amount of polymer is chosen to result in a desired viscosity for the pre-polymerization solution (for example a viscosity compatible with the pre-polymerization solution being able to cover a perforation and not fall through the perforation into the middle ear) and a desired stiffness for the resulting polymer matrix/scaffold/hydrogel after polymerization (for example a stiffness compatible with the material functioning as a scaffold after assembling). In some embodiments, the amount (concentration) of initiator may be chosen based upon irradiation time required for polymerization, wavelength of light source, cell compatibility, and chemical composition. In some embodiments, the total amount of polymer is not so high as to impede or prevent the polymers from assembling into a network and not so low such that the amount of polymer is insufficient to allow network assembly. In some embodiments, the total amount of polymer is chosen to result in a viscous solution rather than a heterogenous paste, which may vary depending upon the specific polymer composition. In some embodiments, the total amount of polymer is about 60 wt % or less (for example when polyhydroxylethylmethacrylate (PHEMA) is used), or about 40 wt % or less (for example when PEG is used), or about 5 wt % or less (for example for some combinations of chitosan/hyaluronic acid). In some embodiments, the total amount of polymer is greater than about 1 wt %. In some embodiments, the total amount of polymer ranges from about 1 wt % to about 60 wt %, or about 1 wt % to about 40 wt %, or from about 1 wt % to about 5 wt %, or from about 5 wt % to about 60 wt % or from about 5 wt % to about 40 wt %, or from about 40 wt % to about 60 wt %.

Methods

In some embodiments, the methods include administering liquid pre-polymer compositions to a desired site in a patient's ear and curing/assembling the compositions in vivo. For example, to administer the compositions to the tympanic membrane, a syringe may be used for delivering the pre-polymerization solution down the narrow ear canal. Alternatively, in some embodiments wherein the pre-polymerization solution is relatively very viscous, it may be applied to a surgical tool such as an ear loop and then administered to the tympanic membrane. For different compositions the administration may vary depending on the mode of polymer assembly. For light-activated networks, in some embodiments, the pre-polymerization solutions are irradiated after placement, for example with a dental during light or any other light source that provides the correct wavelength and intensity specific to the photoinitiator used (e.g. a UV or blue light sensitive gel). Heat sensitive networks may be activated, in some embodiments, by the patient's body temperature upon placement in the ear cavity. pH sensitive gels may be activated, in some embodiments, by the acidic environment in the ear canal following placement. Spontaneously assembling networks may be injected, in some embodiments, via a double-lumen syringe so that the polymer and its initiator are mixed as they are placed at the desired site, for example within the perforation.

In some embodiments, the methods include enhancing existing otologic treatment methods, such as otologic packing materials or patches. For example, in some embodiments, the pre-polymerized solution may be applied to other surgical materials to enhance their effect such as by providing a drug-delivering modality to packing materials. In other or further embodiments, the pre-polymerized solution may be applied to surgical materials to enhance their adhesive character to the native tissue.

EXAMPLES

Examples and methods of use are described herein as a basis for teaching one skilled in the art to employ the invention in any appropriate manner. These examples disclosed herein are not to be interpreted as limiting.

Example 1

In laboratory testing, precursors may comprise poly(ethylene glycol) diacrylate of molecular weight 1000 or poly(ethylene glycol) diacrylate of molecular weight 4000 purchased from Polysciences Inc. (Warrington, Pa.). Albumin from bovine serum (BSA), tetramethylrhodamine conjugate may be purchased from Invitrogen Inc. (Eugene, Oreg.).

Drug incorporation and release were tested. Hydrogels were loaded with BSA during the initial crosslinking procedure. A 10% w/v solution of BSA in PBS with pH 7.4 was prepared. Photocrosslinkable solutions of 10% w/v PEG in PBS with 0.5% Irgacure 2959 photoinitiator were prepared. BSA was incorporated into the solutions at 5 wt % to macromer loading. The final solutions were stirred for 15 minutes at 350 rpm. Then 200 µL was pipetted into wells of a 96 well plate. Each construct was irradiated with UV light for 55 sec. The gels were immediately removed from the wells using a spatula and placed in separate vials containing 5 mL of PBS solution. Then the vials were placed in a shaker at 37° C. (50 rpm). At different time points 500 µL of the PBS solution was removed as a sample and replaced with the same amount of PBS. A Hewlett Packard Diode Array Spectrophotometer (model 8452A) was used to evaluate amount of BSA that was released at each time point.

Example 2

In the clinic, one embodiment of the present invention may comprise the following administration. The patient may be lying down on their side, with their ear under a microscope. This allows the physician to view and work with the tympanic membrane with both hands free. The physician is now able to administer the liquid pre-polymer composition that has been mixed with the desired drugs. The composition can be dropped into the ear with a pipette, much like eardrops are administered. It is likely that the physician will only need tens of microliters of composition to cover the perforation. Once the composition has been added and covers the perforation, the physician can then irradiate the composition with light wherever a hydrogel is needed. Though the unused composition does not need to be aspirated, excess composition may be removed with either a pipette or some absorbent object according to the physician's preference. Any excess of composition can be added to ensure that the perforation is covered by the gel, since all excess composition can be removed. An attachment for the light source (such as a fiber optic cable) may be used to reach the TM of all patients. Since this all takes place under a microscope, the physician is able to be precise in covering the perforation with gel.

Example 3

In a surgical setting, one embodiment of the present invention may comprise enhancing current surgical packing materials for the middle ear. The liquid pre-polymer composition that has been mixed with the desired drugs may be dropped onto the packing material and polymerized with light prior to closing the surgical wound. This embodiment would afford the surgical packing material some antibacterial and drug delivery characteristics that it does not currently possess, in addition to enhanced mechanical support, thus improving the post-surgery prognosis.

Example 4: Experimental Verification

In our lab, we monitored the release of the protein bovine serum albumin (BSA) in two UV-cured PEG hydrogels of different molecular weights over a period of three weeks. The data, shown below in Table 2, indicated that the molecular weight of PEG has a direct relationship with drug release. This study confirmed that the amount of released protein can be controlled by changing the molecular weight of the PEG in the hydrogel, and that PEG hydrogels with higher molecular weight can release more BSA than a lower molecular weight PEG hydrogel over the same period of time. These drug release studies also indicated that the rate of protein release increases slightly during the first two weeks, but the changes during this period are not significant, and the protein release can be controlled to stay within the desired range. The techniques used during this preliminary study can be used for all further drug release studies.

TABLE 2

Mean values and standard deviations of bovine serum albumin release from PEG hydrogels of two different molecular weights over time.

| PEG MW 4000 | | PEG MW 1000 | |
| --- | --- | --- | --- |
| Concentration of released drug in 0.1 ml of PBS (mg/ml), Mean Value | Standard Deviation Of the data | Concentration of released drug in 0.1 ml of PBS (mg/ml), Mean Value | Standard Deviation Of the data |
| Day 2  2.36 | 0.0697 | Day 2  1.12 | 0.0340 |
| Day 4  2.41 | 0.0300 | Day 4  1.60 | 0.0967 |
| Day 6  2.62 | 0.112  | Day 6  1.55 | 0.0286 |
| Day13  2.87 | 0.105  | Day13  1.42 | 0.325  |

FIG. 1 illustrates the histogram of bovine serum albumin released from PEG hydrogels of two different molecular weights over time. As the molecular weight increases, the pore size of the hydrogel network may also increase. This may result in a larger volume of the drug being released over time. Additionally, the degradation rate of the hydrogel may increase. In some embodiments, it may be desirable to optimize both the release rate of the drug, and the degradation rate of the hydrogel network. We have observed that, over a two-month period, the PEG MW 1000 remained intact but the PEG MW 4000 degraded entirely when both were in a PBS solution (37° C., 50 RPM). Therefore, in certain embodiments requiring full degradation in relative speed, it would be preferable to utilize an embodiment with PEG MW 4000 over PEG MW 1000. The degradation rate may increase when the scaffold is in the presence of cells actively remodeling their environment, such as the tympanic membrane. The degradation rate of the scaffold may change when in other tissues because of a difference in pH or native molecules that either speed up or slow down the degradation rate. For example, a change in degradation rate would probably be most obvious in the digestive tract, where the pH is very different from normal body fluid, and many different molecules for degrading different scaffolds are present. As a counter-example, the degradation rate probably will not change in the vitreous of the eye.

Example 5: Synthesis of Reagents

All materials for the remaining examples are from Sigma-Aldrich (St. Louis, Mo.) and used as received unless otherwise stated.
Methacrylation of Chitosan
Chitosan was purified before use. First, a 1 wt % solution of chitosan in 10 vol % acetic acid was vacuum-filtered to remove insoluble particles. Next, the chitosan was precipitated from solution with 1N sodium hydroxide, then centrifuged at 1400 g for 10 min at room temperature. The supernatant was decanted, then water was added in equal volume to the chitosan and the mixture vortexed. The chitosan suspension was dialyzed in water for 2 d, with water changes 3 times/day. After dialysis, the chitosan suspension was lyophilized for 3 d.
Purified chitosan was dissolved in 1 vol % acetic acid. A volume of methacrylic anhydride equal to 5% of the volume of 1% acetic acid was added to the chitosan solution, and the solution was stirred for 3 d at 55° C. The chitosan solution was dialyzed in water for 2 d with water changes 3 times/day. The dialyzed solution was lyophilized for 3 d.
The degree of methacrylation of methacrylated chitosan (MeCS) was determined by proton nuclear magnetic resonance spectroscopy, and determined to be ~40%.
Methacrylation of Hyaluronic Acid
A similar protocol to add a methacrylate group to hyaluronic acid, a naturally occurring polymer that is very amenable to cell growth, was used as described above in connection with the methacrylation of chitosan. Two different versions of methacrylated hyaluronic acid were synthesized: one with ~90% degree of methacrylation (MeHA_90) and one with ~30% (MeHA_30). The synthesis of MeHA took 21 days.

Example 6: Initial Testing of Polymerization Efficacy

Tested polymerization behavior of MeCS and MeHA separately using established system of UV light and UV light-sensitive initiator.
Purpose: Unfamiliar materials tested with known polymerization systems.
Result: Both MeCS and MeHA polymerized into an insoluble polymer network in a predictable manner, with increasing stiffness as irradiation time increased.

Example 7: Formulation of Light-Reactive Materials

Choosing a Material Formulation
In this example, we aimed for a material that could form a polymer network upon exposure to blue light from a dental curing light.
Benefits of using blue light from a curing light may include:
Hand-held curing lights for dental materials are already calibrated for use with living tissue
Light output optimized for blue light-sensitive photoinitiators
User-friendly design
Economical compared to other light sources
Initial Formulation
For the first set of experiments, we tried the same initiator system used with dental materials because:
Reagents are FDA-approved.
Many references are available that characterize the behavior of initiator system.
Dental curing lights are optimized for dental material initiator system.
Reagents:
Camphorquinone (CQ): a blue light-reactive photoinitiator
Ethyl 4-dimethylaminobenzoate (EDMAB): an amine catalyst
2,6-di-tert butyl-4-methyl phenol (BHT): a free-radical inhibitor
Methacrylated chitosan (MeCS)
Methacrylated hyaluronic acid (MeHA_30 and MeHA_90)

Because the blue light-reactive initiator system of CQ/EDMAB is not traditionally used for hydrogel polymerization, we tested several variables as shown in Table 3:

TABLE 3

| CQ:EDMAB | Solvent System | Wt % of Polymers | Irradiation Time |
|---|---|---|---|
| 2:1 | Isopropanol/H$_2$O | 0.5 | 60 s |
| 1:1 | Ethanol/H$_2$O | 1 | 120 s |
| 1:2 | DMSO/H$_2$O | 2 | 180 s |
|  | Acetic acid/H$_2$O | 4 |  |

The solvent system was the main variable to overcome, as neither CQ nor EDMAB are water-soluble.

For these experiments, the solutions, as shown in Table 4, were mixed and pipetted onto glass cover slips. The curing light was mounted in place with a clamp, and the solutions irradiated for specified times. Gelation was evaluated qualitatively.

TABLE 4

Example system.

| Formula | Solvent System | Irradiation Time | Notes |
|---|---|---|---|
| 0.5% MeCS | Isopropanol/H$_2$O | 60 s | Color change upon mixing & medium-stiff gel formation |
| 1.2% CQ 1.2% EDMAB | DMSO/H$_2$O | 60 s | Color change upon mixing % some small gel formation |
| 0.05% BHT | Acetic acid/H$_2$O | 60 s | Some gel formation |

With MeCS, we could get some gel formation using the CQ/EDMAB system. However, we were unable to get similar results with either version of MeHA as shown in Table 5 below.

TABLE 5

Example system.

| Formula | Solvent System | Irradiation Time | Notes |
|---|---|---|---|
| 1.0% MeHA_90 | Acetic acid/H$_2$O | 60 s | No gel formation |
| 1.2% CQ |  | 120 s | No gel formation |
| 1.2% EDMAB |  | 180 s | No gel formation |
| 0.05% BHT |  |  |  |

Altering the solvent system to something other than water inhibited gel formation with MeHA. Due to this, we switched blue-light photoinitiators.

Second Formulation

Riboflavin monophosphate is a water-soluble version of the vitamin riboflavin. It is also a blue-light photoinitiator that has recently been used to polymerize methacrylated long-chain polymers.

Reagents:

Riboflavin 5'-monophosphate sodium salt (RF): blue light-photoinitiator

MeCS

MeHA

For these experiments, the solvent system was no longer a variable to test. These variables were tested as shown in Table 6

TABLE 6

| MeCS/MeHA or HA | Concentration of RF | Wt % of Polymers | Irradiation Time |
|---|---|---|---|
| 2:1 | 10 uM | 1 | 60 s |
| 1:1 | 20 uM | 2 | 120 s |
| 1:2 | 30 uM | 4 | 180 s |

In this experiment, our priority was to get the stiffest gel possible in a reasonable time frame as shown in Table 7 below.

TABLE 7

Example system.

| Formula | Irradiation Time | Gel Formation (Y/N) | Notes |
|---|---|---|---|
| 2% MeCS | 60 s | ~ | Formed sort-of-gel |
| 2% MeHA_90 | 120 s | Y | Stiff gel |
| 30 uM RF | 180 s | Y* | Very stiff gel |

Among the different formulations we tested, as shown in Table 8, we assembled a few that formed very stiff gels. Besides the variables tested here, some additional factors that played a role in gelation were: acidity of solution, light intensity, background color of substrate.

TABLE 8

Formulas that formed stiff gels.

| Formula | Irradiation Time | Notes |
|---|---|---|
| 2% MeCS 2% MeHA_90 30 uM RF | 180 s | Least viscous pre-polymerization solution of the three. |
| 2% MeCS 2% MeHA_30 30 uM RF | 180 s | Moderately viscous pre-polymerization solution. |
| 4% MeCS 30 uM RF | 120 s | Very viscous pre-polymerization solution, but shortest irradiation time required. |

Based upon these results, it appears the formulation with 2% MeCS/2% MeHA_90 may be the easiest to eject from a syringe needle.

Example 8: Determination of Drug Release Profile

Preparation of Gel Patch

Stock solutions were prepared of all reagents and combined to give the final concentrations of the pre-polymerized solution seen in the Table 9 below. Prior to polymerization, the solution had a very viscous consistency, partially due to the association of the positively charged side groups of chitosan and negatively charged side groups of hyaluronic acid (HA).

TABLE 9

Composition of pre-polymerized hydrogel patch material.

| Reagent | Concentration | Purpose |
|---|---|---|
| Methacrylated Chitosan | 2 wt % | Scaffold |
| Hyaluronic Acid | 1 wt % | Scaffold |
| Riboflavin 5'-monophosphate sodium salt | 30 uM | Photoinitiator |
| Ciprofloxacin | 6 mM | Antibiotic |

For all applications of the gel patch, the pre-polymerized solution was irradiated for 3 min using a custom light guide (Leoni, Nuremburg, Germany) fitted to a dental curing light (Mini-Blast, First Medica, Greensboro, N.C.) with a power output of 300 mW/cm$^2$.

Drug Release

To determine the drug release profile of the gel patch, 50 ul volumes of pre-polymerized material were polymerized with blue light. The resulting gels were incubated in 0.5 wt % lysozyme in water. Samples of the solution were taken at 1, 5, 10, and 15 d to determine the cumulative release of ciprofloxacin over time. The ciprofloxacin concentration of the sample solutions was determined with UV-Vis spectrophometry against a standard curve of known ciprofloxacin concentrations.

Figure 2:
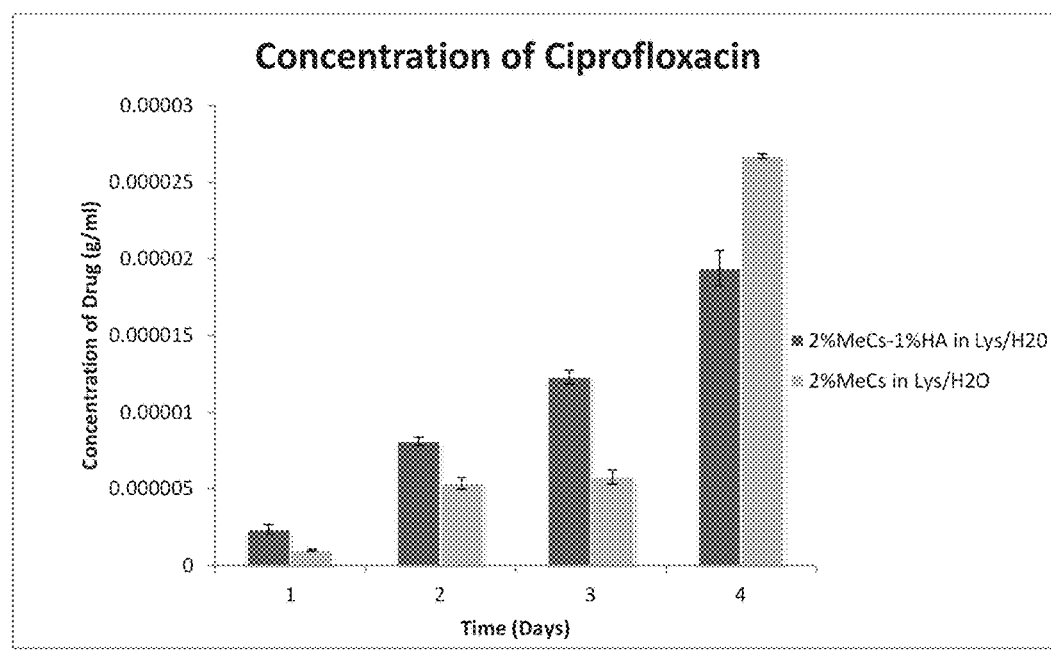
FIG. 2 is a graph illustrating Ciprofloxacin release from 2% MeCS and 2% MeCS/1% HA in 0.5% lysozyme in water.
Figure 3:
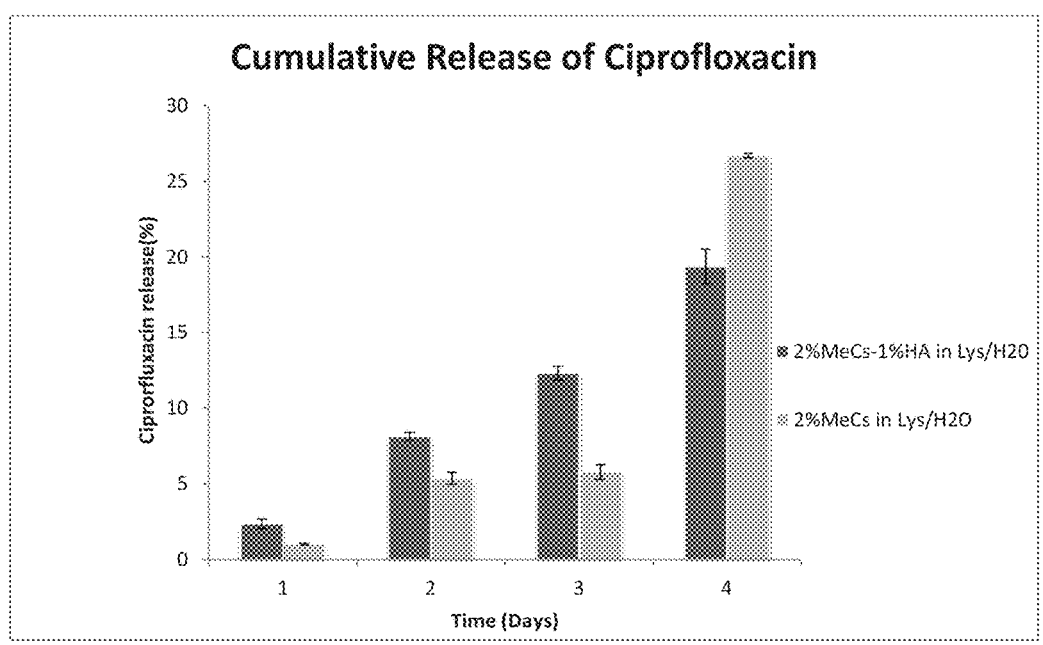
FIG. 3 is a graph illustrating Cumulative release of ciprofloxacin from 2% MeCS and 2% MeCS/1% HA in 0.5% lysozyme in water.

The release of ciprofloxacin was dependent upon the polymer network crosslinking density of the material. In FIG. 2, the release of ciprofloxacin is compared between gels consisting of either 2 wt % MeCS or 2 wt % MeCS/1 wt % HA. Because the gel with both MeCS and HA has a higher crosslink density than the gel with only MeCS, the release of ciprofloxacin was significantly slower. FIG. 3 shows the cumulative release of ciprofloxacin over the course of the study. A slower release profile may be advantageous for the material, as it may extend the time window the perforation has to heal without risk of infection. Neither material demonstrated a "burst release" profile—a sudden release of drugs incongruous with the rest of the release profile—confirming that the release of ciprofloxacin can be controlled by crosslink density.

Example 9: In Vivo Animal Model Establishment and Testing

All in vivo work was performed on adult male chinchillas in accordance with a protocol reviewed and accepted by the Institutional Animal Care and Use Committee.

Induction of Chronic Tympanic Membrane Perforations

A pilot study with 4 adult chinchillas (8 tympanic membranes [TMs]) was conducted to first establish the method for consistently inducing a chronic TM perforation. Tympanic membrane perforations were induced using thermal cautery according to an existing model. See, Amolis C P, Jackler R K, Milczuk H, et al. An animal model of chronic tympanic membrane perforation, Otolarngol Head Neck Surg 1992; 106: 47-55, which is herein incorporated by reference in its entirety. A brass wire wrapped around a soldering iron (Radio Shack, Fort Worth, Tex.) served as a thermal cautery device, and perforations were established in the anterior window of the TM. Perforations were examined weekly, and additional cautery was performed on healed TMs. Perforations that persisted for 30 days were considered to be chronic.

From the pilot study, 75% of perforations induced by thermal cautery persisted for at least 30 days. This method was used to induce perforations in the experimental group of 8 chinchillas. After 30 days, the persistent perforations were comparable in size to what would be present in a human patient receiving the patch.

Application of Material

The pre-polymerized solution of MeCS, HA, riboflavin monophosphate, and ciprofloxacin were mixed in water and loaded into a syringe. The viscous solution was then ejected onto an ear loop and transferred to the perforation. The material was cured using a dental curing light with the custom light guide. Of the experimental group, the gel patch was initially applied to 2 perforations, with 1 perforation used as a control. The gel-patched perforations were monitored weekly, and the healing rate compared to perforations not patched with the material.

Evaluation of Material

The gel patch adhered to the perforation site, and was present 3 weeks after implantation. There was evidence of cell ingrowth within the gel, and there has been no incidence of infection or adverse reaction in animals that received the gel patch. The perforation healed four weeks after the gel application. The study suggests that the material may require four weeks to repair chronic perforations in the TM. The perforation that did not receive the gel patch was still persistent.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

Additional Embodiments

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments, "exemplary" embodiments, or "other" embodiments may include all or part of "some," "other," and "further" embodiments within the scope of this invention. In addition not all embodiments include one or more of the listed objects. For example, materials and methods within the scope of the disclosure can also be defined in accordance with the below embodiments.

1. A scaffold for the promotion of healing tissues in biological organisms wherein the scaffold is initially a liquid and may be cured into a solid; and delivers drugs to promote healing of the perforation.
2. The scaffold of embodiment 1, wherein the scaffold is biodegradable.
3. The scaffold of embodiment 2, wherein the scaffold is for otological use.
4. The scaffold of embodiment 3, wherein the scaffold is for pediatric otological use.
5. The scaffold of embodiment 1, wherein the scaffold provides mechanical support.
6. The scaffold of embodiment 1, wherein the scaffold is used in conjunction with other treatments for healing tissues in biological organisms.
7. The scaffold of embodiment 1, comprising at least one polymer, at least one substance that results in the scaffold turning into a gel when an environmental change is applied.
8. The scaffold of embodiment 7, wherein the scaffold forms a hydrogel.

9. The scaffold of embodiment 8, wherein the scaffold is a photo-polymerizable hydrogel.
10. The scaffold of embodiment 9, wherein the hydrogel polymerizes upon UV light.
11. The scaffold of embodiment 9, wherein the hydrogel polymerizes upon visible light.
12. The scaffold of embodiment 8, wherein the scaffold is a selectively polymerizable hydrogel.
13. The scaffold of embodiment 7, wherein at least one polymer is polyethylene glycol.
14. The scaffold of embodiment 7, wherein at least one polymer is hydrophilic.
15. The scaffold of embodiment 14, wherein at least one polymer is chitosan.
16. The scaffold of embodiment 7, wherein at least one polymer is hyaluronic acid.
17. The scaffold of embodiment 7, further comprising a photoinitiator.
18. The scaffold of embodiment 17, wherein the substance that results in the scaffold turning to a gel when an environmental change is applied is methacrylate.
19. The scaffold of embodiment 17, wherein the substance that results in the scaffold turning to a gel when an environmental change is applied is acrylate.
20. The scaffold of embodiment 17, wherein the photoinitiator is selected from the group: Irgacure 2959, eosin Y in conjunction with 1-vinyl-2-pyrrolidinone and triethanolamine, and riboflavin 5'-monophosphoate salt.
21. The scaffold of embodiment 7, wherein at least one polymer may have a molecular weight between 100 and 1,000,000 g/mol.
22. The scaffold of embodiment 21, wherein at least one polymer has a molecular weight ranging from 1000 g/mol to 4000 g/mol.
23. The scaffold of embodiment 22, wherein at least one polymer has a molecular weight of 4000 g/mol.
24. The scaffold of embodiment 7, wherein at least one polysaccharide has a molecular weight between 100 and 1,000,000 g/mol.
25. The scaffold of embodiment 7, wherein at least one polymer or at least one polysaccharide has deacylation ranging from 0 to 100%.
26. A method of treating a perforation of the tympanic membrane comprising,
administering a liquid pre-polymer composition that has been mixed with desired therapeutics,
covering the perforation with the pre-polymer, and
irradiating the composition with light wherever a hydrogel is needed.
27. The method of embodiment 26, wherein the physician administers tens of microliters of pre-polymer to cover the perforation.
28. The method of embodiment 26, further comprising adding an excess of pre-polymer to ensure that the perforation is covered.
29. The method of embodiment 26, further comprising using an attachment for the light source.
30. The method of embodiment 29, wherein the attachment for the light source is a fiber optic cable.
31. A method of enhancing current otologic packing materials or patches comprising,
administering a packing material to the necessary areas,
administering a liquid pre-polymer composition that has been mixed with desired therapeutics, and
irradiating the composition with light wherever a hydrogel is needed.

What is claimed is:
1. A method of treating a perforation of the tympanic membrane comprising:
 a. administering a liquid pre-polymer composition to the tympanic membrane, the pre-polymer composition comprising: at least a first polymer and a solvent, wherein the liquid pre-polymer composition is sufficiently viscous such that it can be positioned to cover the tympanic membrane perforation without falling through to the middle ear cavity both prior to administration on the tympanic membrane and prior to activation of curing into the polymer matrix and, which when activated in situ in the ear of a patient results in the liquid pre-polymer composition assembling into a polymer matrix suitable for repairing or aiding repair of a tympanic membrane perforation, and further the liquid pre-polymer composition has a viscosity of about 2800 cP or greater; and, thereafter
 b. activating the liquid composition to form a polymer matrix.
2. A method according to claim 1, wherein the liquid pre-polymer composition comprises an initiator.
3. A method according to claim 1, wherein the liquid pre-polymer composition further comprises a therapeutic composition, and the polymer matrix has a porosity and average pore size sufficient to release the therapeutic composition over a desired time period.
4. A method according to claim 1, wherein repairing or aiding the repair comprises assembling the liquid into a polymer matrix stiff enough to function as a scaffold on which epithelial cells of the tympanic membrane can migrate, adhere and grow.
5. A method according to claim 1, wherein the polymer matrix is a hydrogel.
6. A method according to claim 4, wherein the at least first polymer is chosen to result in a functionalized scaffold having a cell-binding domain for improving cell migration and adhesion.
7. A method according to claim 5, wherein the liquid pre-polymer composition comprises an initiator which is a photoinitiator.
8. A method according to claim 7, wherein activating comprises exposing the liquid pre-polymer composition to UV light, visible light or blue light in situ as determined by the photoinitiator.
9. A method according to claim 7 wherein the photoinitiator is chosen from: Irgacure 2959, eosin Y in conjunction with 1-vinyl-2 pyrrolidinone and triethanolamine, camphorquinone, and riboflavin 5'-monophosphate sodium salt.
10. A method according to claim 1, wherein the at least first polymer is chosen from polyethylene glycols (PEG), polysaccharides, poly(lactic acid)s, polyurethanes, poly(propylene glycols), poly(propylene fumarate-co-ethylene glycols), poly(hydroxyethyl methacrylates), polymethyl methacrylates, polyesters, gelatins, alginates, starches, dextrans, polyvinylpyrrolidones, poly(2-acrylamido-2-methyl-1-propanesulfonic acid), polyvinyl alcohols, polypeptides, polyacrylates, agaroses, celluloses, k-carrageenans, pectins, chondroitin sulfates, proteins and derivatives and analogs thereof.
11. A method according to claim 10, wherein the at least first polymer is chosen from PEGs, polysaccharides, and derivatives and analogs thereof.
12. A method according to claim 11, wherein the polysaccharides are chosen from methacrylated chitosans and methacrylated hyaluronic acids.

13. A method according to claim 12, wherein the methacrylated chitosans are at least about 40% methacrylated, and the methacrylated hyaluronic acids are at least about 30% methacrylated.

14. A method according to claim 13, wherein the methacrylated hyaluronic acids are at least about 90% methacrylated.

15. A method according to claim 12, wherein the at least first polymer is methacrylated chitosan, or the at least first polymer is methacrylated hyaluronic acid, or the at least first polymer is chosen from a first polymer which is a methacrylated chitosan and a second polymer which is chosen from a methacrylated hyaluronic acid and hyaluronic acid, or the at least first polymer is a first polymer which is a PEG, a second polymer and optionally a third polymer, wherein the second and third polymer are chosen from chitosans and hyaluronic acids.

16. A method according to claim 10, wherein the at least first polymer has molecular weight ranging from about 100 to about 1,000,000 g/mol.

17. A method according to claim 16, wherein the at least first polymer has a molecular weight ranging from about 1000 to about 4000 g/mol.

18. A method according to claim 1, wherein the at least first polymer is a chitosan having deacylation ranging from about 0% to about 100%.

19. A method according to claim 1, wherein the liquid pre-polymer composition has a viscosity of about 3000 cP or greater.

20. A method according to claim 1, wherein the liquid composition further comprises a photoinitiator, and activating comprises exposing the liquid pre-polymer composition to a light source chosen from UV light, visible light, infrared light and blue light according to the photoinitiator to cause the liquid composition to assemble to form a polymer matrix.

21. A method according to claim 1, wherein administering comprises providing a sufficient amount of liquid pre-polymer to the site of the perforation to cover the perforation.

* * * * *